United States Patent [19]

Grime

[11] 4,132,883
[45] Jan. 2, 1979

[54] ELECTRIC STEAM VAPORIZER

[75] Inventor: Thomas E. Grime, Toledo, Ohio

[73] Assignee: Champion Spark Plug Company, Toledo, Ohio

[21] Appl. No.: 695,541

[22] Filed: Jun. 14, 1976

[51] Int. Cl.$^2$ .......................... H05B 3/60; F22B 1/30; A61L 9/02

[52] U.S. Cl. .................... 219/284; 422/299; 128/192; 219/275; 219/289; 219/314; 239/136; 261/142

[58] Field of Search ............................ 219/271–276, 219/284–295, 314; 128/192; 239/136; 21/117–119; 261/141, 142

[56] References Cited

U.S. PATENT DOCUMENTS

| | | | |
|---|---|---|---|
| 1,534,079 | 4/1925 | Russell et al. | 219/290 |
| 2,454,657 | 11/1948 | Kuzmin et al. | 219/276 |
| 2,519,515 | 8/1950 | Turner | 219/274 |
| 2,542,529 | 2/1951 | Hunt | 219/276 X |
| 2,763,765 | 9/1956 | Duberstein et al. | 219/289 X |
| 3,610,879 | 10/1971 | Katzman et al. | 219/271 |
| 3,659,078 | 4/1972 | Rudstrom | 219/273 X |
| 3,714,392 | 1/1973 | Katzman et al. | 219/284 |
| 3,743,780 | 7/1973 | Camp | 219/273 X |
| 3,971,913 | 7/1976 | Myklebust | 219/275 X |

Primary Examiner—A. Bartis
Attorney, Agent, or Firm—Oliver E. Todd, Jr.

[57] ABSTRACT

An improved electric steam vaporizer having a container defining a liquid reservoir and a removable cover for the container. Two parallel electrodes depend into the liquid reservoir from a cap attached to the cover. The electrodes are attached to the cap by inserting into electrode-receiving openings formed in the cap, welding the conductor ends on a line cord to tabs which project through the cap, bending the tab to mechanically lock the electrodes to the cap and in one embodiment potting the tabs and line cord conductor ends with a sealing material. An electrode housing attached to the cap surrounds the electrodes to define an inner-boiling chamber, an outer water-filled insulating chamber, and a small volume annular surge chamber which surrounds the lower end of the boiling chamber. The surge chamber which has an opening into the boiling chamber and an open bottom communicating with the liquid reservoir, reduces hot water flow from the boiling chamber to the reservoir and cold water flow from the reservoir to the boiling chamber. Steam from the boiling chamber passes through a foam trapping intermediate chamber in the cap and is discharged from a steam outlet which extends through the cap and the cover.

6 Claims, 8 Drawing Figures

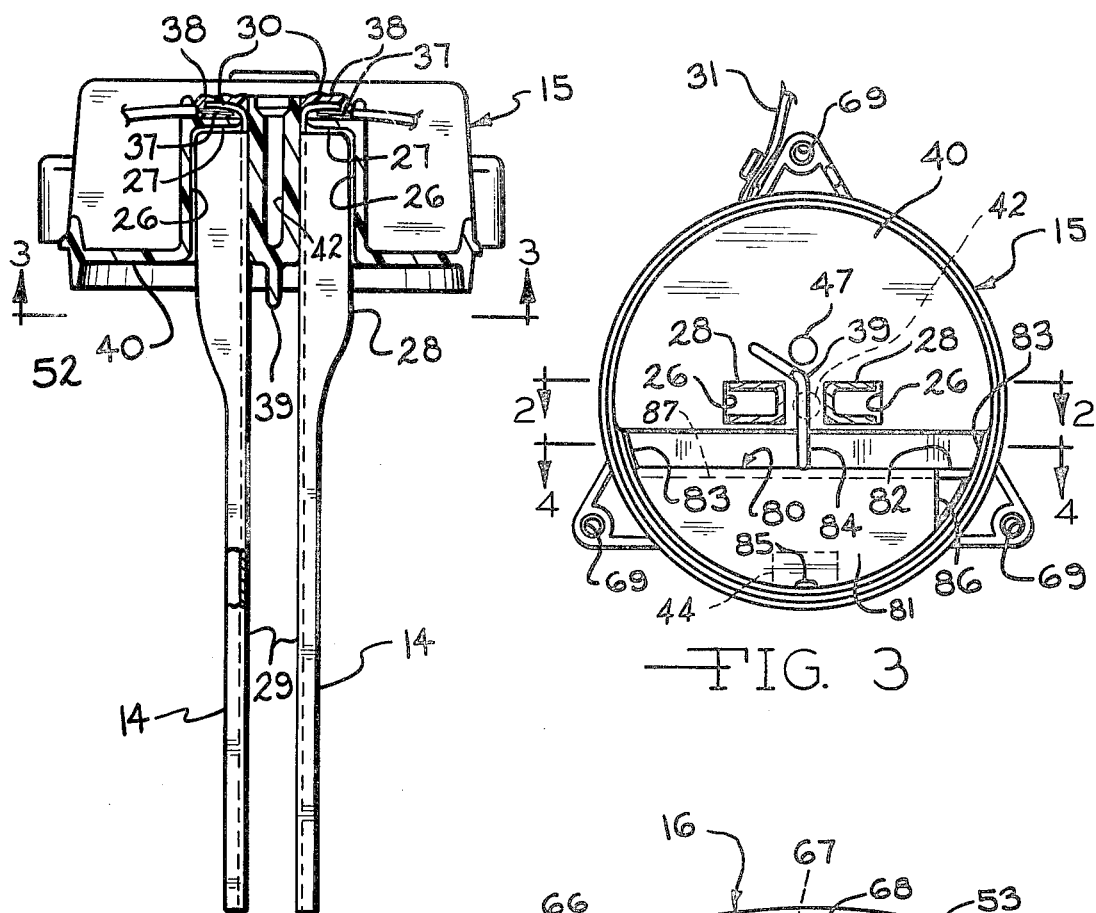
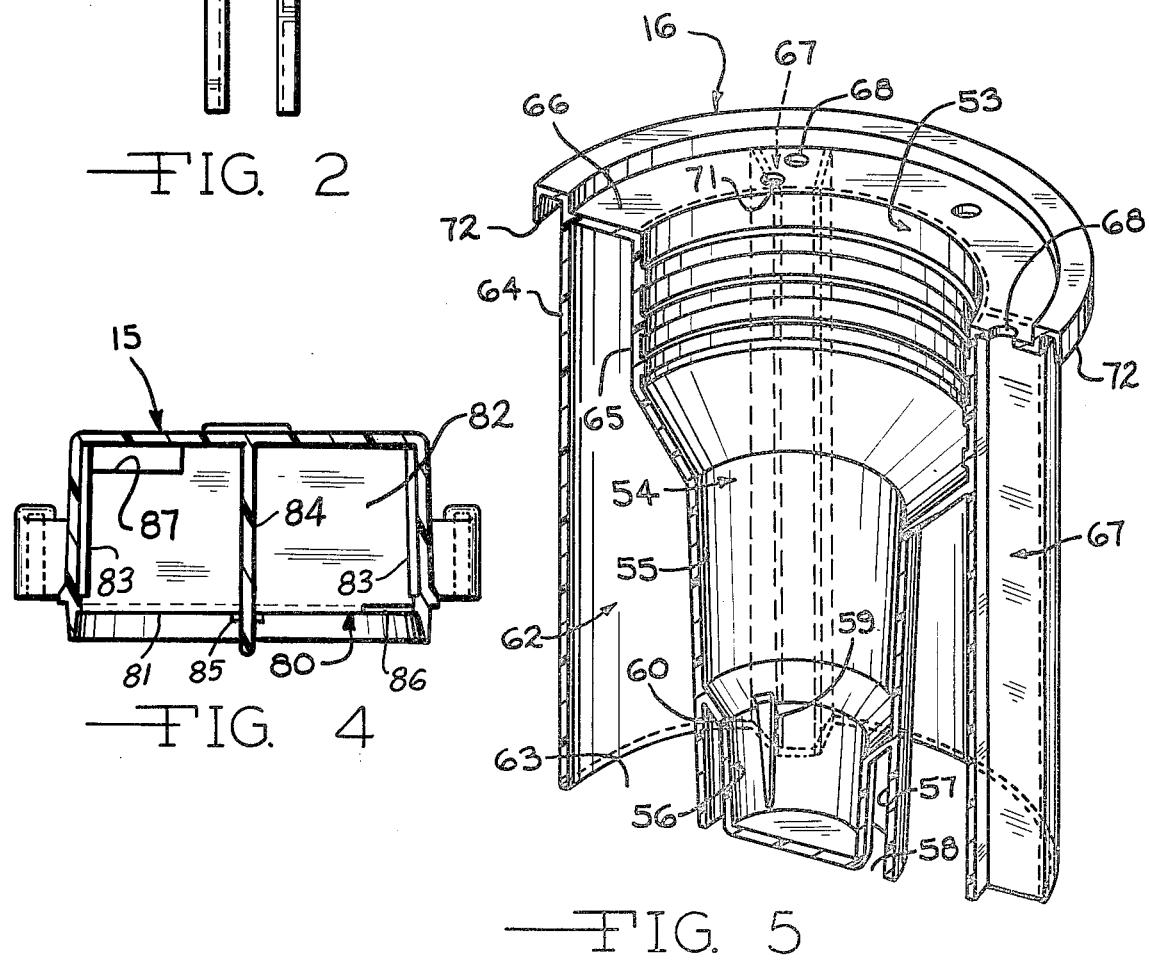

ELECTRIC STEAM VAPORIZER

BACKGROUND OF THE INVENTION

This invention relates to steam vaporizers and more particularly to improvements in steam vaporizers of the type in which an electric current is passed through a liquid such as water to heat the liquid to its boiling point for generating steam.

Steam vaporizers are commonly used in sick rooms to relieve colds, bronchitis, and other respiratory ailments. Often, such vaporizers are used in the home, for example, in the bedrooms of small children. Steam vaporizers are also sometimes used as a room humidifier. A common type of electric steam vaporizer includes a pair of parallel electrodes which are mounted to extend into a water reservoir. An electric current is passed between the electrodes to heat the water for generating steam. The electrodes are commonly surrounded with a cylindrical tube for defining a boiling chamber having an appriciably smaller volume than the reservoir. However, there has been difficulty in confining the heat to the boiling chamber in prior art vaporizer designs. There is considerable hazard to a patient using the vaporizer when water in the reservoir or receptical at a location exterior to the boiling chamber becomes very hot after prolonged use. One solution to this problem has been to provide an annular air or water-filled insulating chamber between the boiling chamber and the liquid reservoir. The boiling chamber is then completely enclosed, except for a small opening into the reservoir to permit replenishment water to flow into the boiling chamber. However, there is still considerable heat transferred from the boiling chamber to the reservoir due to a liquid surging action through the replenishment water opening. Water surges back and forth between the boiling chamber and the reservoir while the vaporizer is operated. This surging action causes heated water from the boiling chamber to enter the reservoir, thereby increasing the temperature of the water in the reservoir. Also, cooler reservoir water enters the boiling chamber to lower the efficiency of the boiling chamber.

Another problem with prior art steam vaporizers of this type is the erratic occurrence of "spitting" or, in other words, the emission of hot water droplets along with the steam. This is undesirable since the water droplets are commonly hot enough to cause burns and the steam vaporizers are often used to relieve respiratory problems in children and invalids. It has been found that spitting can be caused by a build-up of foam on the water surface above the boiling chamber caused by minerals and other impurities within the water. In the past, spitting sometimes has been prevented by adding anti-foaming agents to the water in the vaporizer. By destroying surface tension, foam generation is prevented which, in turn, eliminates spitting. However, the use of anti-foaming agents results in additional expense and additional maintenance steps must be taken by the operator of a steam vaporizer.

In the past, steam vaporizers have generally been constructed from a relatively hard synthetic resinous material, such as a phenolic resin. However, materials of this type are relatively expensive compared to some softer thermoplastic materials. It is desirable to manufacture steam vaporizers from softer synthetic resinous materials such as polypropylene to reduce the cost of the vaporizers. However, materials such as polypropylene flow easily under pressure. As a consequence, it is difficult to mount the electrodes in a vaporizer formed from polypropylene so that the electrodes are maintained in a fixed, parallel relationship while heated to the boiling point of water. Prior art techniques for mounting electrodes in a vaporizer with screws or bolts are not acceptable in a vaporizer formed from polypropylene, for example, due to its flow characteristics which may permit the electrodes to move from their parallel relationship and may permit compression type electrical connections to loosen.

SUMMARY OF THE INVENTION

According to the present invention, two parallel electrodes are mounted in a steam vaporizer formed from an inexpensive polypropylene material. The electrodes are mounted in a cap by insertion into passageways which extend through the cap until a tab projects past a partition and from the opposite side of the cap. The ends of a line cord are resistance welded to the tabs and the tabs are bent over to restrain the electrodes from movement in the cap. Through this technique, the electrodes are mounted permanently in a parallel relationship. The electrodes do not exert pressure on the cap, the soft thermoplastic cap material will not flow to permit the electrodes to move out of the parallel relationship or to lose electrical contact.

The electrodes are surrounded by a housing which defines an inner boiling chamber and another, water-filled insulating chamber. On the side of the electrodes housing adjacent to the bottom of the boiling chamber, a water inlet is formed. A small volume annular surge chamber surrounds the water inlet and the lower portion of the boiling chamber. The outlet from the boiling chamber communicates with the surge chamber, which in turn, opens at its bottom into the water reservoir. Hot water surging from the boiling chamber through the water inlet passes into the surge chamber, rather than directly into the main reservoir. When the water surges back through the water inlet into the boiling chamber, hot water from the surge chamber enters the boiling chamber, rather than the cooler reservoir water. Through the use of the surge chamber, heat transfer between the boiling chamber and the main reservoir is greatly reduced over prior art vaporizers.

As steam is generated in the vaporizer boiling chamber, it passes upwardly through the cap to an outlet, where it is discharged from the vaporizer. A baffle is positioned within the cap to define an intermediate chamber through which the steam must pass to travel from the boiling chamber to the steam outlet. The steam outlet is sufficiently large as to maintain the intermediate chamber at substantially atmospheric pressure. Any foam entering the intermediate chamber has an opportunity to subside before reaching the region of the steam outlet. Steam entrances are provided at both the top and bottom of the intermediate chamber so that when foam is present within the chamber, steam may enter through the top opening and pass directly to the steam outlet without passing through the foam and resulting in spitting from the vaporizer.

Accordingly, it is an object of the invention to provide an improved electric steam vaporizer of the type having two parallel electrodes extending into a body of liquid in a boiling chamber for passing current through the liquid to generate steam.

Other objects and advantages of the invention will become apparent from the following detailed description, with reference being made to the accompanying drawings.

BRIEF DESCRIPTION OF THE DRAWINGS

FIG. 2 is a cross-sectional elevational view taken along line 2—2 in FIG. 3; showing the method in which electrodes are mounted in a cap for an electric steam vaporizer heating element according to the present invention;

FIG. 3 is a cross-sectional view taken along line 3—3 of FIG. 2;

FIG. 4 is a cross-sectional view taken along line 4—4 of FIG. 3;

FIG. 5 is a perspective view, in section, of an electrode housing for use in an electric steam vaporizer according to the present invention;

DESCRIPTION OF THE PREFERRED EMBODIMENTS

Figure 1:
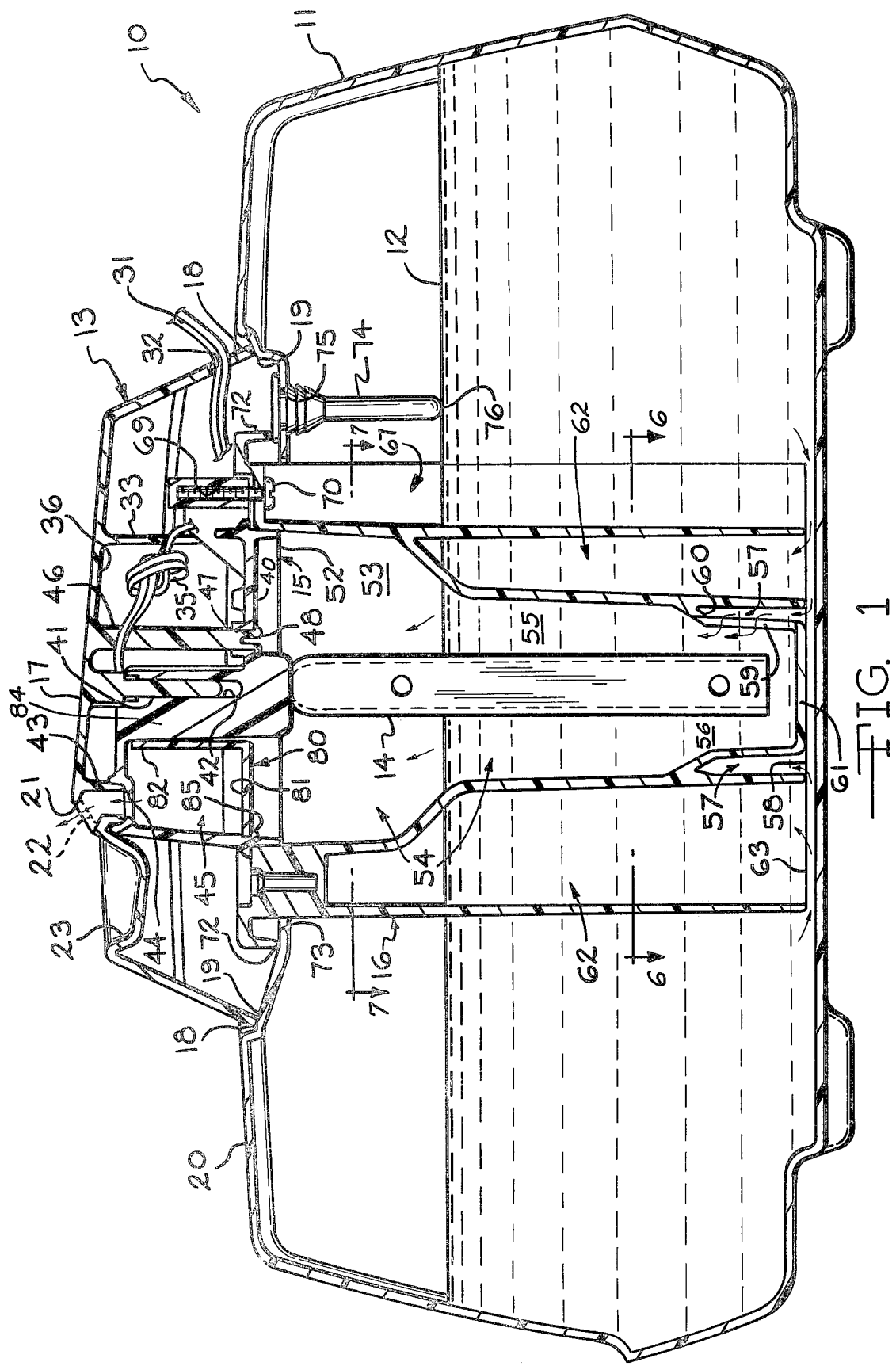
FIG. 1 is a cross-sectional elevational view of an electric steam vaporizer constructed in accordance with a preferred embodiment of the present invention.
Figure 6:
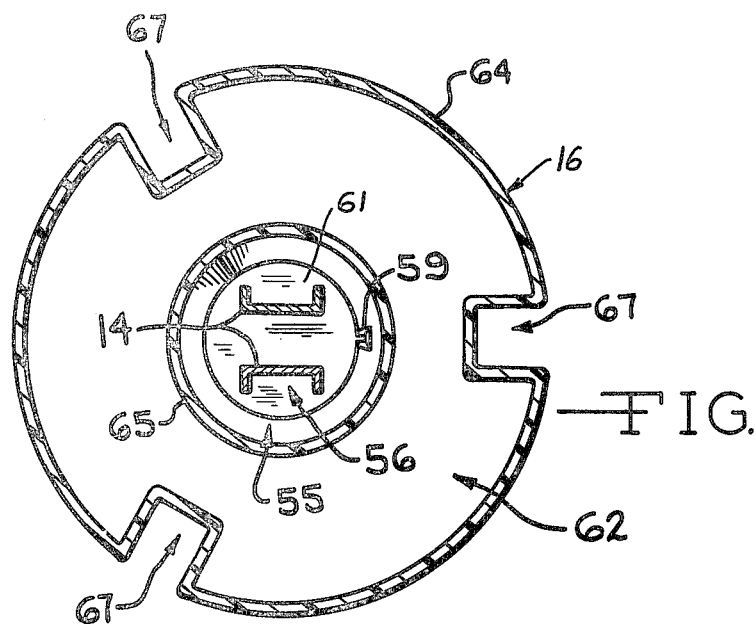
FIG. 6 is a cross sectional view taken along line 6—6 of FIG. 1.
Figure 7:
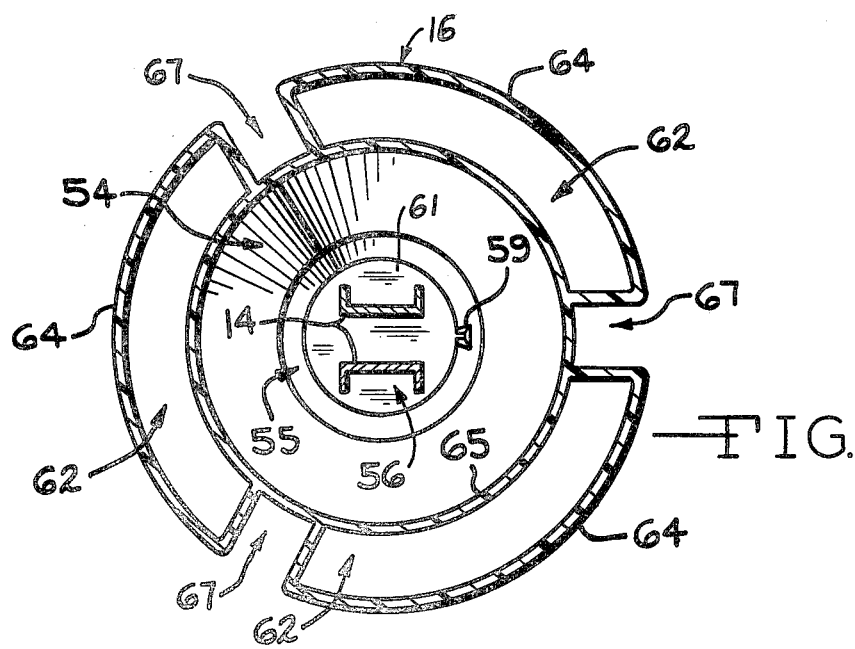
FIG. 7 is a cross sectional view taken along line 7—7 of FIG. 1.

Turning now to the drawings, and particularly to FIG. 1, an electric steam vaporizer 10 is shown in accordance with a preferred embodiment of the invention. The vaporizer 10 generally includes a reservoir or container 11 which holds a body of water 12, or other suitable liquid, to be vaporized and a heating element 13 which converts the water 12 to steam. The heating element 13 includes a pair of electrodes 14 which are mounted on a cap 15. An electrode housing 16 is also attached to the cap 15 to completely enclose the electrodes 14 for preventing a user of the vaporizer 10 from accidently contacting the electrodes 14. The cap 15 is in turn attached to a cover 17 for the container 11.

Figure 8:
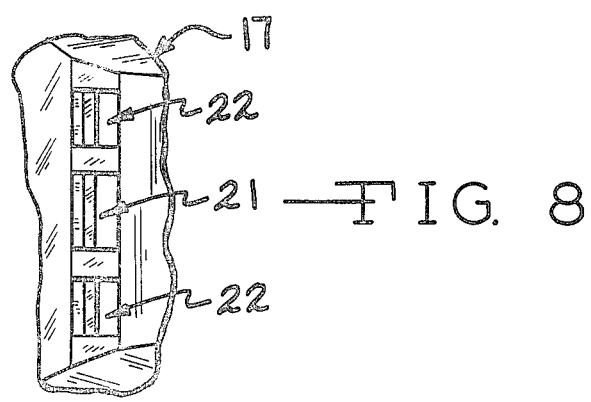
FIG. 8 is a fragmentary top plan view showing the steam outlet and the vent openings.

The cover 17 includes lower edges 18 which are shaped to rest upon a recessed surface 19 formed in an upper surface 20 of the container 11. A steam outlet 21 is formed in the cover 17 and one or more vent openings 22 are formed in the cover 17 adjacent the steam outlet 21, as shown in FIGS. 1 and 8. The vent openings 22 communicate through the cover 17 for providing atmospheric pressure air within the container 11. Immediately in front of and below the steam outlet 21, a cup 23 is formed within the cover 17 for holding a suitable medicament, when desired.

The electrode mounting cap 15 is shown in detail in FIGS. 1 through 4. The cap 15 is molded from an inexpensive synthetic resinous material such as polypropylene. Two parallel openings 26 are molded in the cap 15 for mounting the electrodes 14. The upper end of each of the openings 26 are partially closed by partition 27. The electrodes 14 are stamped from flat sheets of stainless steel, or other corrosion-resistant material, to have a U-shaped cross section to prevent bending. The electrodes 14 each include an upper end 28 adapted to slide longitudinally into the cap recesses 26. When the upper electrode ends 28 of the electrodes 14 are seated within the cap openings 26 and against the partitions 27, the electrodes 14 are restrained from lateral movement and extend with inner surfaces 29 in spaced-parallel relationship. The upper electrode ends 28 closely engage the walls of the cap openings 26 to prevent lateral movement of the electrodes 14 from their parallel relationship. A tab 30 projects from the upper end 28 of each electrode 14 for mechanically retaining the electrodes 14 within the openings 26 and for making electrical connections to the electrodes 14. A two conductor line cord 31 extends through an opening 32 through the vaporizer cover 17 and through an opening defined between a shroud 33 and the cap 15. The shroud 33, which is molded integrally with the cover 17, encloses a portion of the cap 15 to define a chamber 36. A strain relief knot 35 is tied in the line cord 31 and is positioned within the chamber 36. The line cord 31 has two conductor ends 37 which are connected to the electrode tabs 30 by means of conventional welding techniques. Through the use of welding, a metal-to metal bond is formed between the conductor ends 37 and the tabs 30. After the conductor ends 37 are welded to the electrode tabs 30, the tabs 30 are bent over to abut the cap partitions 27, thereby retaining the electrodes 14 within the the cap opening 26. A mass of silicone sealing compound 38 is then placed over the tabs 30, the conductor ends 37 and the partitions to electrically insulate and to form a water-tight seal between the conductor ends 37, the tabs 30 and the cap 15. Of course, other suitable potting compounds may also be used. A rib 39 is formed to project from a lower surface 40 of the cap 15. The rib 39 extends between and to either side of the space between the electrodes 14 for increasing the minimum surface paths on the cap 15 between the two spaced electrodes 14. The rib 39 is of importance since the lower cap surface 40 is exposed to steam generated in the vaporizer 10. By increasing the surface path over the cap 15 between the electrodes 14, current passing between the electrodes through condensed steam on the cap 15 is decreased considerably to prevent excessive heating of the cap 15. Also electrical arcing along the surface of the cap 15 between the electrodes 14 is minimized. It will be noted that only the lower surface 40 of the cap 15 is exposed to steam. The cap 15 is disposed between the steam and the chamber 36 and isolates the line cord 31 from the steam.

After the electrodes 14 are attached to the cap 15 and the line cord 31, the cap 15 is attached to the container cover 17. The cap 15 and the cover 17 are fitted together with a pin 41 on the cover 17 pressed into a blind opening 42 formed in the cap 15. The pin 41 and the opening 42 function to align the cap 15 with the cover 17 so that a tube 43 molded in the cover 17 connects the steam outlet 21 with an opening 44 into a chamber 45 formed in the cap 15. The cover 17 also includes a pin 46 which extends through and projects from an opening 47 in the cap 15. A projecting end 48 of the pin 46 is then hot staked to permanently connect the cap 15 and the cover 17 together.

Turning to FIGS. 1 and 5–7, the electrode housing 16 is shown in detail. A tapered annular shoulder 52 which depends from around the outside of the bottom 40 of the cap 15 seats within an upper section 53 of a boiling chamber 54 defined by the electrode housing 16. The boiling chamber 54 encloses the electrodes 14 for limiting the mass of water adjacent the electrodes 14. The upper boiling chamber section 53 has a relatively large diameter and the diameter of the boiling chamber 54 tapers to an intermediate section 55 and then to a smaller diameter lower section 56. The electrodes 14 extend substantially to the bottom of the lower section 56. An annular surge chamber 57 surrounds the lower boiling chamber section 56. The surge chamber 57 has an open bottom 58 which allows water to flow between the surge chamber 57 and the main body of water 12 in the container 11. A side opening 59 is also provided between the surge chamber 57 and the lower boiling chamber section 56 to permit water flow between these chambers. Although the side opening 59 may have various configurations, it is preferably of a V-shape and extends substantially to an upper region 60 of the surge chamber 57. During operation of the vaporizer 10, the body of water 12 within the container 11 will tend to seek its own level and will flow through the surge chamber bottom opening 58 and the side opening 59 into the boiling chamber 54. When electrical power is applied to the line cord 31 to cause water within the chamber 54 to boil, a small amount of the water will surge through the side opening 59 into and out of the boiling chamber 54. In one direction, water surges from the boiling chamber 54 into the surge chamber 57, forcing water to flow from the surge chamber 57 through the bottom outlet 58. This water will tend to rise into an insulating chamber 62 which surrounds the boiling chamber 54 and the surge chamber 57, as will be discussed below. In a reverse direction, water flows from the body of water 12 through the bottom opening 58 into the surge chamber 57 forcing water in the surge chamber 57 to flow through the side opening 59 into the boiling chamber 54. By providing the side opening 59 with a V-shape which extends substantially to the upper region 60 of the surge chamber 57, the major flow of hot water from the boiling chamber 54 will pass through the larger area at the top of the opening 59 into the upper region 60 of the surge chamber 57. Since the hot water tends to rise due to its lower density, it will remain in the upper region 60 of the surge chamber 57. During reverse flow, the hot water in the upper region 60 of the surge chamber 57 flows back through the opening 59 into the boiling chamber 54. The major portion of the flow of hot water is confined to the upper region 60 of the surge chamber 57 due to the significantly greater area of the V-shaped side opening 59 adjacent the upper region 60 than the area adjacent the bottom opening 58.

Normally, it would be preferable to confine the side opening 59 only to the upper region 60 of the surge chamber 57. However, such an arrangement would prevent all of the water from draining from the boiling chamber 54 when the heating element 13 is removed from the container 11. For this reason, the opening 59 extends downwardy to a bottom portion 61 of the boiling chamber 54. It should be appreciated that the opening 59 must be sufficiently large as to permit relatively rapid draining of the boiling chamber 54 when the heating element 13 is removed from the container 11. For example, it is desirable to have the boiling chamber 54 drain completely in no more than three of four seconds. On the other hand, if the opening 59 is too large, excessive heat will be transferred to the body of water 12 in the container. Also, the electrodes 14 will be exposed to an operator of the vaporizer during maintenance. Of course, the opening 59 may have various other configurations. For example, the opening 59 may have a generally rectangular shape, or the single opening 59 shown may be replaced with one or more holes providing a relatively large area connecting the upper surge chamber region 60 with the lower boiling chamber section 56 and also one or more holes having an appreciably smaller area connecting the surge chamber 57 and the boiling chamber 54 adjacent the bottom 61. By providing the major flow area adjacent near the upper surge chamber region 60, hot water surges back and forth between the boiling chamber 54 and the upper region 60 of the surge chamber 57 and cooler water surges between the body of water 12 in the container 11 and the surge chamber 57. In this arrangement, heat transfer between the boiling chamber 54 and the body of water 12 resulting from the surging action through the opening 59 is greatly reduced over prior art steam vaporizers.

The electrode housing 16 also defines an insulating chamber 62 which surrounds at least the intermediate section 55 and the lower section 56 of the boiling chamber 54. The insulating chamber 62 is provided with an annular bottom opening 63 which allows the water 12 in the container 11 to flow into the insulating chamber 62. Once water enters the chamber 62, it will act as an insulating layer between the chamber 54 and the main body of water 12 in the container 11. Also, any hot water expelled from the bottom opening 58 of the surge chamber 57 will tend to rise through the opening 63 into the chamber 62 rather than heating the main body of water 12. An outer wall portion 64 defining the outer surfaces of insulating chamber 62 and an inner wall portion 65 between the insulating chamber 62, the surge chamber 57 and the boiling chamber 54 are connected together by an annular web or flange 66. A plurality of longitudinal recesses or slots 67 are defined by the outer wall 64, as shown in FIGS. 1, 5, 6 and 7. A screw hole 68 extends through the web 66 in the region immediately above each slot 67. The screw holes 68 in the web 66 align with threaded openings 69 in the cap 15. Three such threaded openings 69 are located in the cap 15, as shown in FIG. 3. During assembly of the heating element 13, the electrodes 14 are mounted in the cap 15, the cap 15 is attached to the cover 17 and the electrode housing 16 is positioned with the tapered shoulder 52 on the cap 15 seated within the upper boiling chamber section 53. Screws 70 are then passed through the screw holes 68 and threaded into the cap opening 69 to connect the electrode housing 16 to the cap 15. By using screws to connect the electrode housing 16 to the cap 15, the electrode housing 16 may be removed at a later date for cleaning mineral deposits from the electrodes 14.

One or more vent holes 71 are provided in the web 66 to vent both the container 11 and the insulating chamber 62. A single vent hole 71 is shown in FIG. 5 positioned to communicate both with one of the longitudinal slots 67 for venting the container 11 and with the insulating chamber 62. The vent hole 71 communicates through voids between the cap 17, the cover 15 and the container 11 to the vent openings 22 through the cap 17 for maintaining the interior of the container 11 and the interior of the insulating chamber 62 at atmospheric pressure. The electrode housing also includes a downwardly directed annular flange 72 which extends from the web 66 and is of a diameter larger than a container opening 73 which passes the outer portion 64 of the electrode housing 16. When the heating element 13 is positioned on the container 11, the electrode housing 16 extends through the opening 73, except for the flange 72 which engages the recessed upper surface 19 of the container 11 along with the cover 17.

A fill level indicator 74 is mounted within another opening 75 in the recessed upper container surface 19. The fill level indicator 74 is a rod positioned to extend downwardly into the container 11 such that a lower tip 76 is readily visible when the heating element 13 is removed from the container 11. In use, the steam vaporizer 10 is filled with water 12 until the water 12, at most, contacts the lower tip 76 of the fill level indicator 74. The heating element 13 is then positioned on the container 11 so that the electrodes 14 and the electrode housing 16 extends through the opening 73 and into the body of water 12. If desired, a medicament is then added to the cup 23 formed in the cover 17 and, finally, the line cord 31 is connected to an alternating current power source. When the heating element 13 was positioned on the container 11, the cover vent 22 and the vent 71 in the electrode housing web 66 allowed the water 12 to flow through the bottom opening 63 into the insulating chamber 62 and through the surge chamber 57 and the side opening 59 into the boiling chamber 54 until such water achieves the same level as the water in the container 11. When power is applied to the line cord 31, current flows through the water between the electrodes to heat such water to boiling. The steam generated from the boiling water passed upwardly through the cap 15 and the steam outlet 21 in the cover. As steam discharges from the outlet 21, vapors from any medicament in the cover cup 23 are entrained and disbursed by the flowing steam. Since the cap 15 is disposed between the chambers 45 and 54 and the chamber 36, steam is prevented from flowing into the chamber 36.

Steam flowing through the cap 15 passes through the intermediate chamber 45 which is defined by the cap 15 and a baffle 80, as best seen in FIGS. 1, 3, and 4. The baffle 80 generally comprises a horizontal bottom 81 and a vertical side 82. The bottom 81 is somewhat semicircular in shape while the side 82 is generally rectangular in shape. When the baffle 80 is positioned within the cap 15, two stops 83 and an extension 84 on the rib 39 molded in the cap 15 restrained the baffle side 82 from movement while a detent 85 locks the baffle bottom 81 in position. A relatively small steam opening 86 is formed in the baffle bottom 81 and a steam opening 87 is formed at the top of the baffle side 82 to provide two paths of communication between the boiling chamber 54 and the intermediate chamber 45. Steam generated from the boiling water will normally pass through both openings 86 and 87 into the intermediate chamber 45 and from the chamber 45 through the opening 44 and the steam outlet 21 and discharge into the atmosphere. In the event that mineral content in the water 12 is sufficiently high as to produce foam in the boiling chamber 54, the foam will form water droplets which will condense and settle to the bottom of the chamber 45 while steam passes through the upper opening 87 and the chamber 45 to the steam outlet 21. This is because the water droplets will be carried only from the primary outlet from the boiling chamber, which is into the intermediate chamber 45 rather than the steam outlet 21. Thus, the intermediate chamber 45 functions to keep water droplets produced by foam away from the opening 44 and the steam outlet 21 to greatly reduce the possibility of water "spitting" from the steam outlet 21.

After operation of the steam vaporizer 10, it is desirable to rinse out the container 11 and to rinse the electrode housing 16 and electrodes 14 to minimize mineral buildup. Since some water will be in the container 11 after a use, it is desirable to have water drain as rapidly as possible from the electrode housing 16 as the heating element 13 is removed from the container 11. The vent 71 functions to permit a rapid draining of the insulating chamber 62 and, similarly, the steam passage vents the boiling chamber 54. Furthermore, the side opening 59 adjacent the bottom 61 of the boiling chamber 54 also is designed to permit rapid draining. Not only is this desirable for convenience of the user, but it is also necessary for safety purposes. The line cord 31 should be disconnected from the power source prior to removing the heating element 13 from the container 11. However, through negligence or carelessness, a user may forget to disconnect the line cord. It should be appreciated that water retained within the boiling chamber 54 will be in contact with the electrodes 14. Therefore, for safety purposes, the boiling chamber 54 must drain as rapidly as possible, and, preferably, within only a few seconds from when the heating element is lifted from the container 11.

Although various improvements have been described in a preferred embodiment of a steam vaporizer 10, it will be appreciated that various modifications and changes may be made without departing from the spirit and scope of the following claims.

What I claim is:

1. An improved electric steam vaporizer comprising, in combination, a container for holding a body of liquid, a heating means including a pair of substantially parallel spaced elongated electrodes, means for mounting said heating means on said container with said electrodes extending downwardly into such body of liquid to adjacent a bottom of said container, means for applying an alternating current potential to said electrodes whereby liquid between said electrodes is heated to boiling by passage of current through the liquid, housing means surrounding said electrodes for defining a liquid boiling chamber, said heating means including means for discharging steam from said boiling chamber to the atmosphere, said housing means including a sidewall extending downwardly to substantially the bottom of said container and a closed bottom connected to said sidewall, means defining a surge chamber surrounding a lower portion of said sidewall adjacent said housing bottom, said surge chamber having bottom opening means communicating with such body of liquid in said container and a closed upper end, and side openings means connecting at least an upper portion of said surge chamber adjacent said upper end with said boiling chamber for flowing heated liquid surging from said boiling chamber to primarily the upper portion of said surge chamber and downwardly towards said bottom opening means thereby forcing cooler liquid from said surge chamber into such body of liquid and for providing heated liquid from said upper portion of said surge chamber to flow into said boiling chamber.

2. An improved electric steam vaporizer, as set forth in claim 1, wherein said side opening means extends from substantially the top of said surge chamber to substantially said housing means bottom, and wherein said side opening means has a substantially larger area adjacent the top of said surge chamber than adjacent said housing means bottom.

3. An improved electric steam vaporizer, as set forth in claim 2, wherein said side opening means is V-shaped.

4. An improved electric steam vaporizer, as set forth in claim 3, wherein said housing means further includes means defining an insulating chamber surrounding said boiling chamber and said surge chamber.

5. An improved electric steam vaporizer, as set forth in claim 4, wherein said means for discharging steam from said boiling chamber to the atmosphere includes a steam outlet for discharging steam to the atmosphere, a hollow intermediate chamber having a top, bottom and sidewall, means connecting said steam outlet to said intermediate chamber through said top of said intermediate chamber, first opening means in said bottom of said intermediate chamber connecting said intermediate chamber and said boiling chamber, and second opening means in said intermediate chamber sidewall adjacent said top of said intermediate chamber connecting said intermediate chamber and said boiling chamber.

6. An improved electric steam vaporizer, as set forth in claim 1, wherein said means for discharging steam from said boiling chamber to the atmosphere includes a steam outlet for discharging steam to the atmosphere, a hollow intermediate chamber having a top, bottom and sidewall, means connecting said steam outlet to said intermediate chamber through said top of said intermediate chamber, first opening means in said bottom of said intermediate chamber connecting said intermediate chamber and said boiling chamber, and second opening means in said intermediate chamber sidewall adjacent said top of said intermediate chamber connecting said intermediate chamber and said boiling chamber.

* * * * *